United States Patent [19]

Harrison et al.

[11] 4,391,818
[45] Jul. 5, 1983

[54] 4-(SUBSTITUTED ALKYL)-N-(1,3-DITHIOLAN-2-YLIDENE(ANILINE

[75] Inventors: Boyd L. Harrison, Cincinnati; Niall S. Doherty, West Chester, both of Ohio

[73] Assignee: Merrell Dow Pharmaceuticals Inc., Cincinnati, Ohio

[21] Appl. No.: 367,540

[22] Filed: Apr. 12, 1982

[51] Int. Cl.³ ............... A61K 31/385; C07D 339/06
[52] U.S. Cl. .................................. 424/277; 549/38
[58] Field of Search ......................... 424/277; 549/38

[56] References Cited
U.S. PATENT DOCUMENTS

| | | | |
|---|---|---|---|
| 4,004,019 | 1/1977 | Brand et al. | 424/277 |
| 4,060,628 | 11/1977 | Enders et al. | 424/277 |
| 4,131,683 | 12/1978 | Harrison et al. | 424/277 |
| 4,172,941 | 10/1979 | Harrison et al. | 544/28 |

Primary Examiner—Richard Raymond
Attorney, Agent, or Firm—John J. Kolano; Gary D. Street; Raymond A. McDonald

[57] ABSTRACT

N-(1,3-dithiolan-2-ylidene)-4-alkylanilines having a hydroxy, alkoxy or alkanoyloxy substituent on the alkyl group are useful as anti-inflammatory agents, as analgesic agents and as antiasthmatic agents. The compounds involved can be prepared by the reaction of an appropriate 4-alkylaniline with a methyl(1,3-dithiolan-2-ylidene)sulfonium salt or with carbon disulfide and ethylene dibromide in the presence of a base.

10 Claims, No Drawings

4-(SUBSTITUTED ALKYL)-N-(1,3-DITHIOLAN-2-YLIDENE(ANILINE

The present invention relates to N-(1,3-dithiolan-2-ylidene)anilines having a substituted alkyl group at the 4-position. The substituent on the alkyl group is hydroxy or a hydroxy derivative. More particularly, the present invention relates to compounds having the following general formula

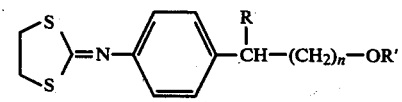

wherein R is hydrogen or lower alkyl of 1–6 C; R' is hydrogen, lower alkyl of 1–6 C, or lower alkanoyl of 2–6 C; and n is 0–10. The present invention further encompasses the pharmaceutically acceptable acid addition salts of the above compounds.

The lower alkyl groups referred to above contain 1–6 carbon atoms. Examples of such lower alkyl groups are methyl, ethyl, propyl, isopropyl, butyl, and hexyl. The lower alkanoyl groups referred to above contain 2–6 carbon atoms and can be exemplified by acetyl, propionyl, butyryl, and hexanoyl.

The pharmaceutically acceptable acid addition salts are equivalent to the free bases for the purposes of the present invention. Illustrative of such salts are salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic, and like acids; and with organic sulfonic acids such as methanesulfonic acid and 4-toluenesulfonic acid.

As examples of compounds of the present invention are the following:
2-[4-(1,3-dithiolan-2-ylideneamino)phenyl]ethanol.
4-[4-(1,3-dithiolan-2-ylideneamino)phenyl]butanol.
8-[4-(1,3-dithiolan-2-ylideneamino)phenyl]octanol.
2-[4-(1,3-dithiolan-2-ylideneamino)phenyl]propanol.
N-(1,3-dithiolan-2-ylidene)-4-[1-(ethoxymethyl)propyl]aniline.
N-(1,3-dithiolan-2-ylidene)-4-(6-ethoxyhexyl)-aniline.
N-(1,3-dithiolan-2-ylidene)-4-(6-butoxyhexyl)-aniline.
N-(1,3-dithiolan-2-ylidene)-4-[1-(propionyloxymethyl)propyl]aniline.
N-(1,3-dithiolan-2-ylidene)-4-(6-butyryloxyhexyl)-aniline.

A preferred embodiment of the present invention are those compounds wherein R' is hydrogen or lower alkanoyl. A further preferred embodiment are those compounds wherein R' is lower alkanoyl. A still further preferred embodiment of the present invention are those compounds wherein R is hydrogen.

To obtain the compounds of the present invention, methyl(1,3-dithiolan-2-ylidene)sulfonium iodide is reacted with a substituted aniline of the formula

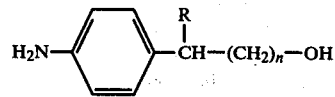

wherein n and R are defined as above. The reaction is carried out at room temperature in an inert solvent such as dimethylformamide in the presence of a tertiary amine such as triethylamine. The alcohol thus obtained can then be converted to the ethers and esters of the present invention by standard procedures. Thus, reaction of the product alcohol with a strong base such as sodium hydride gives the corresponding alcohol salt which is then reacted with an alkyl halide or similar compound to give the ether. If the product alcohol described above is reacted with an acid halide, preferably the chloride, or an acid anhydride by standard procedures, the corresponding ester is obtained. Alternatively, it is possible to obtain the desired ethers and esters by use of the appropriate ether- or ester-substituted aniline in the general procedure described earlier.

Although the general procedure described above involved the use of methyl(1,3-ditholan-2-ylidene)sulfonium iodide because that material can be obtained readily, it is also possible to use other S-alkyl derivatives or other salts of the indicated compound when it may be convenient or advantageous to do so.

Alternatively, the compounds of the present invention can be prepared by reaction of the appropriate substituted aniline with carbon disulfide and a base followed by reaction with ethylene dibromide to give the desired product. The base used can be potassium carbonate or a similar compound. In the process, the amine first reacts with the carbon disulfide to give the corresponding dithiocarbamate salt which then further reacts with ethylene dibromide to give the dithiolane ring structure.

The substituted anilines used in the procedure described above can be prepared by standard procedures. Most conveniently, a benzenealkanoic acid is nitrated to give the corresponding 4-nitrophenyl compound which is reduced stepwise (first with a reducing agent such as borane-dimethylsulfide complex to reduce the carboxylic acid group to an alcohol, followed by catalytic reduction to convert the nitro group to an amino group) to give the desired starting materials for use in the present invention. Using various appropriate combinations of reactions, the corresponding ether and ester starting materials can also be obtained. While the above nitration procedure is generally quite satisfactory, it suffers from the disadvantage that nitration gives some polynitrated products and nitro isomers which must be removed to give the pure intermediate. Alternatively, one can start with 4-nitrobenzaldehyde, react that with an appropriate substituted ylide to give a 4-nitro(substituted alkenyl)benzene, and then reduce the various unsaturated groups by standard procedures to give the desired material. While this procedure does involve an additional step, it avoids the purification problems of the other procedure.

The compounds of the present invention are useful as anti-inflammatory agents, analgesic agents, and as anti-asthmatic agents. More specifically, as anti-inflammatory agents, the present compounds are useful in the treatment of painful inflammation conditions such as rheumatoid arthritis or osteoarthritis or also dental pain. The present compounds would also be useful in the treatment of dysmenorrhea. While all of the compounds of the present invention are useful for the purposes indicated above, the alcohols and esters are preferred as anti-inflammatory agents whereas the ethers are preferred as antiasthmatic agents. The esters are particularly preferred as anti-inflammatory agents because prolonged use of common anti-inflammatory agents commonly cause stomach ulceration but the present esters produce only a low degree of stomach ulceration.

The activities of the present compounds were determined by standard test procedures. Thus, anti-inflammatory activity was demonstrated by the carrageenan paw edema test. Groups of male Sprague-Dawley rats were starved overnight before dosing with the test compounds. The ordinary initial screening dose is 100 mg/kg. One hour after dosing, 0.05 ml of 1% carrageenan was injected into the left-hind paw of the animals and swelling was measured 3 hours later. Animals were then autopsied and the stomach examined for the presence of ulcers. When the compounds of the present invention were tested by the above procedure, they were found to reduce the paw swelling and are thus active anti-inflammatory agents.

A further indication of anti-inflammatory activity was demonstrated by the adjuvant arthritis test in the rat. Arthritis was induced by injection of heat-killed Mycobacterium tuberculosis into the tail of Sprague-Dawley rats. When the disease had fully developed 15 days later, the animals were weighed, the hind-paw volumes determined, and dosing with test compound initiated. The measurements were repeated after 8 daily doses. The reduction in paw volume demonstrates activity in this procedure. The alcohols of the present invention were particularly active in this test.

Analgesic activity for the present compounds was demonstrated by the acetic acid writhing test. The method was a modification of the procedure of Whittle [Brit. J. Pharmacol., 22, 246 (1964)]. Groups of 5 to 10 mice were administered one or more doses of test compound by the route desired (except intraperitoneal). At a selected time thereafter, acetic acid (0.4 ml of a 0.25% v/v solution) was administered intraperitoneally to the mice. Starting 5 minutes later, the animals were observed for a period of 15 minutes for the appearance of abdominal writhing and the number of squirms for each mouse was counted. Analgesia was considered significant in those mice which did not squirm during the 15 minute observation period. To determine the $ED_{50}$, 4 or more doses were tested in groups of 10 mice. The compounds of the present invention were active when tested by the above procedure.

The antiasthmatic activity of the compounds of the present invention was determined by inhibition of SRSA biosynthesis in vitro. In this procedure, rat peritoneal cells were incubated at 37° C. in Hanks' balanced salt solution containing indomethacin (1 $\mu$g/ml) and various concentrations of test compound for 30 minutes before adding calcium ionophore. After a further 15 minutes incubation, the reaction was stopped, the SRS extracted and bioassayed. The indomethacin was present during the incubation to block formation of prostaglandins which could interfere with the bioassay. When tested by the above procedure, the present compounds were found to inhibit SRS biosynthesis.

The anti-inflammatory and antiasthmatic agents of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The compositions used may be in the form of tablets, capsules, dragees, gelules, granules, suppositories, injectable solutions or suspensions, pomades, creams, gels and aerosol preparations formed in the usual fashion. Examples of suitable excipients are talc, gum arabic, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and preservatives.

The present invention also includes novel methods of treating inflammation, pain and asthma in mammals which comprises administering to warm-blooded animals an effective amount of at least one compound of the invention. The dosage administered will, of course, vary depending upon known factors such as the pharmacodynamic characteristics of the particular agent, and its mode and route of administration; age, health and weight of the recipient; nature and extent of the symptoms, kind of concurrent treatment, frequency of treatment, and the effect desired. Usually, for anti-inflammatory purposes, a daily dosage of active ingredient can be about 0.5 to 500 milligrams per kilogram (preferable, 5 to 100 milligrams per kilogram) of body weight per day in the adult by the oral route. The active ingredient can be given in a single daily dose, in divided doses 2 to 4 times a day, or in sustained release form to obtain desired results.

The following examples are set forth to illustrate the preparation of compounds employed in the present invention but should not be construed as limiting it in any way.

EXAMPLE 1

A solution of 33.9 g of 2-phenylbutyric acid in 340 ml of concentrated sulfuric acid was cooled to $-10°$ C. with stirring. To this solution was added, dropwise, a mixture of 39.4 ml of 70% nitric acid and 170 ml of acetic acid at such a rate that the temperature was maintained below 0° C. The mixture was then warmed to 20° C. over a period of 1 hour and poured into ice water. The off-white solid which formed was separated by filtration, washed with ice water and sucked as dry as possible on the filter. The resultant solid was dissolved in chloroform, a water layer was separated, and the chloroform layer was dried over magnesium sulfate. The solvent was removed under reduced pressure to give a crude solid which was recrystallized from a mixture of hot toluene/hexane to give 2-(4-nitrophenyl)-butyric acid.

EXAMPLE 2

6-Phenylhexanoic acid (30 g) was added dropwise over 6.5 hours to 125 ml of 90% nitric acid with cooling to $-30°$ to $-20°$ C. When the addition was complete, the mixture was allowed to warm to $-10°$ C. for 30 minutes and it was then poured into ice water. The resulting mixture was extracted with diethyl ether and the ether extract was washed with water and saturated aqueous sodium chloride solution and dried over magnesium sulfate. The solvent was then evaporated to leave a crude yellow solid which was subjected to high pressure liquid chromatography using ethyl acetate/hexane/glacial acetic acid as the eluent. This chromatography removed dinitrated material and gave a yellow slush which was recrystallized from a mixture of toluene and hexane to give 6-(4-nitrophenyl)hexanoic acid.

EXAMPLE 3

To a solution of 20.9 g of 2-(4-nitrophenyl)butyric acid in 500 ml of dry tetrahydrofuran was added, dropwise, 1.1 equivalents of 10 M borane-dimethylsulfide complex in 100 ml of dry tetrahydrofuran. The mixture was stirred at room temperature for 1.5 hours and then refluxed for 1.5 hours and finally cooled to room temperature. Methanol (10 ml) was added, the mixture was stirred for 30 minutes, and the solvent was then evaporated under reduced pressure. The residue was dissolved in 100 ml of methanol and the solvent was evaporated and this procedure was repeated three (3) times. The resulting oil was purified by chromatography on silica gel, eluting with 1:1 ethyl acetate/hexane to give 2-(4-nitrophenyl)butanol as a light-yellow oil.

EXAMPLE 4

To a solution of 9.1 g of 6-(4-nitrophenyl)hexanoic acid in 200 ml of dried tetrahydrofuran was added, dropwise, a solution of borane-dimethyl sulfide complex (0.042 mole) in 40 ml of dried tetrahydrofuran. The resulting mixture was stirred at room temperature for 16 hours and then heated at reflux for 1 hour before it was cooled again to room temperature. Water (10 ml) was added, the mixture was stirred for 15 minutes, most of the solvent was removed, and water was added to the residue. The resultant aqueous mixture was extracted with diethyl ether and the extract was washed with aqueous saturated sodium bicarbonate solution, water, and aqueous saturated sodium chloride solution and dried over magnesium sulfate. The solvent was then evaporated to leave 6-(4-nitrophenyl)hexanol as a yellow oil.

EXAMPLE 5

To a mixture of 2.2 g of sodium hydride (as a 50% oil dispersion) and 15.5 g of methyl iodide in 300 ml of dried dimethylformamide, there was added dropwise a solution of 7.1 g of 2-(4-nitrophenyl)butanol in 100 ml of dimethylformamide. The resulting mixture was stirred at room temperature for 20 hours and then poured into an aqueous solution containing 0.2 M potassium hydrogen phosphate/potassium dihydrogen phosphate buffer solution (pH 7). The resulting mixture was extracted several times with diethyl ether and the combined organic extracts were washed with aqueous dilute sodium thiosulfate solution, water, and aqueous saturated sodium chloride solution, and dried over magnesium sulfate. Evaporation of the solvent gave a red oil which was purified by chromatography on silica gel and elution with ethyl acetate/hexane to give 4-[1-(methoxymethyl)-propyl]nitrobenzene.

EXAMPLE 6

A solution was prepared from 12.9 g of 2-(4-nitrophenyl)butanol and 250 ml of absolute ethanol, 0.65 g of 10% palladium on charcoal catalyst was added and the mixture was hydrogenated in a Parr apparatus at about 2.7 atmospheres for 2 hours. The catalyst was removed by filtration and the solvent was evaporated from the filtrate to leave a crude oil which was purified by kugelrohr distillation (115° C. at 0.2 mm pressure) to give 2-(4-aminophenyl)butanol as a clear-white liquid.

EXAMPLE 7

To a solution of 6.5 g of 4-[1-(methoxymethyl)-propyl]nitrobenzene in 125 ml of ethanol was added 0.32 g of 10% Pd/C catalyst and the resulting mixture was shaken under hydrogen (2.7-3.3 atmospheres) at room temperature for 2 hours. The catalyst was removed by filtration and the solvent was evaporated from the filtrate to give a crude orange oil which was purified by kugelrohr distillation (68°-69° C., 0.005-0.007 mm of mercury). This gave 4-[1-(methoxymethyl)propyl]aniline as a light-yellow oil.

EXAMPLE 8

A solution was prepared from 8.5 g of 6-(4-nitrophenyl)hexanol and 150 ml of ethanol and 0.42 g of 10% Pd/C catalyst was added. The resulting mixture was shaken under hydrogen (2.7-3.3 atmospheres) at room temperature for 2 hours. The catalyst was then removed by filtration and the solvent was evaporated from the filtrate to leave a crude tan solid. The solid was recrystallized from ethyl acetate/hexane to give 6-(4-aminophenyl)hexanol.

EXAMPLE 9

To 450 ml of dimethylformamide containing 23.8 ml of triethylamine was added 11.4 g of 2-(4-aminophenyl)butanol and to the resulting solution was added, in portions over 45 minutes, 21 g of methyl(1,3-dithiolan-2-ylidene)sulfonium iodide. The resulting hazy-yellow solution was stirred for 2 hours and then poured into ice water. The aqueous mixture was extracted 5 times with diethyl ether and the combined organic extracts were washed 7 times with 0.2 N hydrochloric acid, twice with water and once with saturated aqueous sodium chloride solution and dried over magnesium sulfate. The solvent was evaporated and the resulting crude residue was purified by chromatography on silica gel, eluting with 1:1 ethyl acetate/hexane. The purified light-yellow oil obtained was immediately dissolved in warm diethyl ether and allowed to crystallize. The solid which formed was separated by filtration and dried to give 2-[4-(1,3-dithiolan-2-ylideneamino)phenyl]butanol as white spars melting at about 98.5°-100.5° C. This compound has the following structural formula

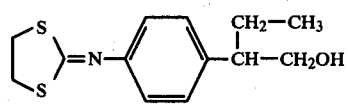

EXAMPLE 10

To a solution of 5.1 g of 4-[1-(methoxymethyl)propyl]aniline and 210 ml of dried dimethylformamide was added 7.25 g of triethylamine. Then, 8.8 g of methyl(1,3-dithiolan-2-ylidene)sulfonium iodide was added and the mixture was allowed to stir at room temperature for 3 hours. The mixture was then poured into water and the resulting aqueous mixture was extracted with 2:1 diethyl ether/ethyl acetate. The organic extract was washed with 0.2 N hydrochloric acid until all unreacted aniline had been removed as shown by thin-layer chromatography. The organic solution was then washed with water and aqueous saturated sodium chloride solution and dried over magnesium sulfate. The solvent was then removed to leave a crude yellow oil which was purified by flash chromatography using silica gel with ethyl acetate/hexane as eluant. The yellow oil obtained was N-(1,3-dithiolan-2-ylidene)-4-[1-(methoxymethyl)propyl]aniline and it was dissolved in 250 ml of diethyl ether. To this solution was added dropwise a solution of 2 g of sulfuric acid in 110 ml of diethyl ether. When the addition was complete, the resulting mixture was placed in a freezer. The solid which formed was separated by filtration and recrystallized from acetonitrile to give N-(1,3-dithiolan-2-ylidene)-4-[1-(methoxymethyl)propyl]aniline dihydrogen sulfate as small white crystals melting at about 134°–137.5° C.

EXAMPLE 11

To a mixture of 3 g of 2-[4-(1,3-dithiolan-2-ylideneamino)phenyl]butanol and 1.25 g of triethylamine in 50 ml of dried methylene chloride was added dropwise a solution of 0.88 g of acetyl chloride in 25 ml of methylene chloride. The resulting solution was stirred at room temperature for 3 hours. It was then washed once with 0.1 N hydrochloric acid, twice with water, and once with saturated aqueous sodium chloride solution and dried over magnesium sulfate. The solid was removed to leave a crude orange oil which was purified by flash chromatography using 15 cm of silica gel and ethyl acetate/hexane as eluant. This gave a colorless oil which was 4-[1-(acetoxymethyl)propyl]-N-(1,3-dithiolan-2-ylidene)aniline. This oil was dissolved in 150 ml of diethyl ether and there was added dropwise a solution of 1.2 g of sulfuric acid in 75 ml of diethyl ether. When the addition was complete, the mixture was placed in a freezer. The precipitate which formed was separated by filtration and recrystallized from acetone/diethyl ether to give 4-[1-(acetoxymethyl)propyl]-N-(1,3-dithiolan-2-ylidene)aniline dihydrogen sulfate as white platelets melting at about 128.5°–131° C. The free base of this compound has the following structural formula

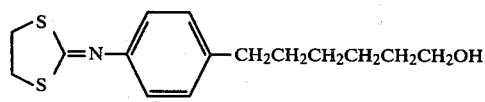

EXAMPLE 12

To a solution of 6.4 g of 6-(4-aminophenyl)hexanol in 255 ml of dried dimethylformamide was added 8.34 g of triethylamine. Then 10.1 g of methyl(1,3-dithiolan-2-ylidene)sulfonium iodide was added portionwise over a period of 1 hour. When the addition was complete, the reaction mixture was allowed to stir at room temperature for 3 hours. It was then poured into water and the aqueous mixture was extracted with diethyl ether. The ether extract was washed with 0.2 N hydrochloric acid until no unreacted aniline remained as shown by thin-layer chromatography. The ether solution was then washed with water and aqueous saturated sodium chloride solution and dried over magnesium sulfate. The solvent was then removed to leave a viscous orange oil which was purified by flash chromatography using 15 cm of silica gel with ethyl acetate/hexane as eluant.

This gave 6-[4-(1,3-dithiolan-2-ylideneamino)phenyl]hexanol as a light-yellow oil. A portion of the oil (1.5 g) was dissolved in 70 ml of diethyl ether and to the resulting solution was added dropwise a solution of 0.55 g of sulfuric acid in 30 ml of diethyl ether. When the addition was complete, the reaction mixture was placed in a freezer. The precipitate which formed was separated by filtration to give an off-white powder which was 6-[4-(1,3-dithiolan-2-ylideneamino)phenyl]-hexanol dihydrogen sulfate melting at about 117°–118° C. with decomposition. The free base of this compound has the following structural formula

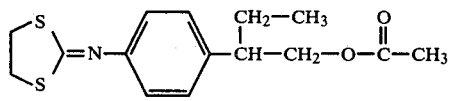

EXAMPLE 13

To a mixture of 0.97 g of sodium hydride and 5.7 g of methyl iodide in 40 ml of dried dimethylformamide was added dropwise a solution of 2.4 g of 6-[4-(1,3-dithiolan-2-ylideneamino)phenyl]hexanol in 25 ml of dimethylformamide. The resulting mixture was stirred at room temperature for 16 hours and then poured into an aqueous solution containing 0.2 M potassium hydrogen phosphate/potassium dihydrogen phosphate buffer solution (pH 7) with a few crystals of sodium thiosulfate added. This aqueous mixture was extracted with diethyl ether and the organic extract was then washed with water and aqueous saturated sodium chloride solution and dried over magnesium sulfate. The solvent was then removed to leave a crude orange oil which was purified by flash chromatography using 15 cm of silica gel and ethyl acetate/hexane as the eluant. The yellow oil obtained was N-(1,3-dithiolan-2-ylidene)-4-(6-methoxyhexyl)-aniline and 1.76 g of the oil was dissolved in 75 ml of diethyl ether. To this solution was added dropwise a solution of 0.6 g of sulfuric acid in 35 ml of diethyl ether. When the addition was complete, the mixture was placed in the freezer. The precipitate which formed was separated by filtration and crystallized from acetonitrile to give N-(1,3-dithiolan-2-ylidene)-4-(6-methoxyhexyl)aniline dihydrogen sulfate as white crystals melting at about 141°–142.5° C.

EXAMPLE 14

To a mixture of 1 g of 6-[4-(1,3-dithiolan-2-ylideneamino)phenyl]hexanol and 0.38 g of triethylamine in 20 ml of dried methylene chloride was added dropwise a solution of 0.27 g of acetyl chloride in 10 ml of dried methylene chloride. The resulting solution was stirred at room temperature for 2 hours. It was then washed with 0.1 N hydrochloric acid, twice with water, and once with aqueous saturated sodium chloride solution and then dried over anhydrous magnesium sulfate. The solvent was then removed to give a crude yellow oil which was purified by flash chromatography using 15 cm of silica gel and ethyl acetate/hexane as the eluant. This gave a colorless oil which was 4-(6-acetoxyhexyl)N-(1,3-dithiolan-2-ylidene)aniline. This oil was dissolved in 40 ml of diethyl ether and there was added dropwise a solution of 0.29 g of sulfuric acid and 20 ml of diethyl ether. When the addition was complete, the reaction mixture was placed in a freezer. The precipitate which formed was separated by filtration and recrystallized from acetonitrile/ethyl acetate to give 4-(6-acetoxyhexyl)-N-(1,3-dithiolan-2-ylidene)-aniline dihydrogen sulfate as white needles melting at about 151.5°–153.5° C. The free base of this compound has the following structural formula

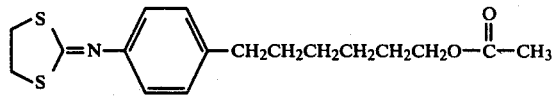

EXAMPLE 15

A solution was prepared from 13.6 g of 1,3-dithiolane-2-thione (ethylenetrithiocarbonate) in 25 ml of reagent nitromethane and 14.2 g of methyl iodide was added dropwise at room temperature with stirring under an atmosphere of nitrogen. The reaction mixture was wrapped with foil for protection from light and stirring was continued for 16 hours. The crystals that formed were separated by filtration, washed with dry benzene and dried *in vacuo* to give methyl(1,3-dithiolan-2-ylidene)sulfonium iodide as brown crystals melting at about 80°–83° C.

What is claimed is:

1. A compound of the formula

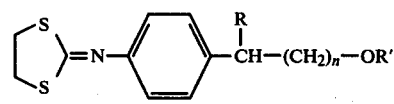

wherein R is hydrogen or lower alkyl of 1–6 C; R' is hydrogen, lower alkyl of 1–6 C, or lower alkanoyl of 2–6 C; and n is 0–10; and the pharmaceutically acceptable acid addition salts thereof.

2. A compound according to claim 1 which has the formula

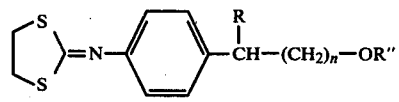

wherein R is hydrogen or lower alkyl of 1–6 C; and R" is hydrogen or lower alkanoyl of 2–6 C; and n is 0–10.

3. A compounds according to claim 1 which has the formula

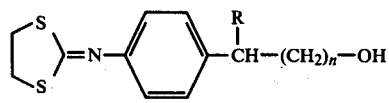

wherein R is hydrogen or lower alkyl of 1–6 C; and n is 0–10.

4. A compound according to claim 1 which is 2-[4-(1,3-dithiolan-2-ylideneamino)phenyl]butanol.

5. A compound according to claim 1 which is 6-[4-(1,3-dithiolan-2-ylideneamino)phenyl]hexanol.

6. A compound according to claim 1 which is 4-(6-acetoxyhexyl)-N-(1,3-dithiolan-2-ylidene)aniline.

7. A compound according to claim 1 which has the formula

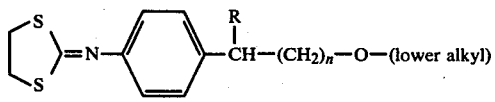

when R is hydrogen or lower alkyl of 1–6 C; and n is 0–10.

8. A compound according to claim 1 which is N-(1,3-dithiolan-2-ylidene)-4-(6-methoxyhexyl)aniline.

9. A method of treating inflammation which comprises administering to a patient in need thereof an effective amount of a compound of the formula

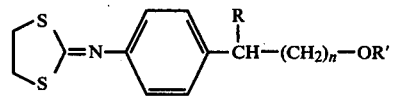

wherein R is hydrogen or lower alkyl of 1–6 C; R' is hydrogen, lower alkyl of 1–6 C or lower alkanoyl of 2–6 C; and n is 0–10; and the pharmaceutically acceptable acid addition salts thereof.

10. A method of treating asthma which comprises administering to a patient in need thereof an effective amount of a compound of the formula

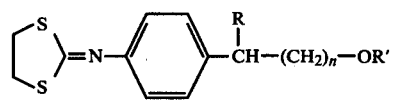

wherein R is hydrogen or lower alkyl of 1–6 C; R' is hydrogen, lower alkyl of 1–6 C or lower alkanoyl of 2–6 C; and n is 0–10; and the pharmaceutically acceptable acid addition salts thereof.

* * * * *